(12) United States Patent
Harada et al.

(10) Patent No.: US 10,928,354 B2
(45) Date of Patent: Feb. 23, 2021

(54) AMMONIA SENSOR ELEMENT

(71) Applicant: DENSO CORPORATION, Kariya (JP)

(72) Inventors: Toshihiko Harada, Nishio (JP); Shinya Teranishi, Nishio (JP); Satoshi Nakamura, Nishio (JP); Hiroaki Yoto, Kariya (JP)

(73) Assignee: DENSO CORPORATION, Kariya (JP)

( * ) Notice: Subject to any disclaimer, the term of this patent is extended or adjusted under 35 U.S.C. 154(b) by 263 days.

(21) Appl. No.: 15/852,115

(22) Filed: Dec. 22, 2017

(65) Prior Publication Data

US 2018/0180569 A1    Jun. 28, 2018

(30) Foreign Application Priority Data

Dec. 26, 2016    (JP) .............................. JP2016-251595

(51) Int. Cl.
*G01N 27/407* (2006.01)
*G01N 27/30* (2006.01)
*G01N 33/00* (2006.01)

(52) U.S. Cl.
CPC ....... *G01N 27/4074* (2013.01); *G01N 27/304* (2013.01); *G01N 33/0054* (2013.01)

(58) Field of Classification Search
None
See application file for complete search history.

(56) References Cited

U.S. PATENT DOCUMENTS

| 5,401,372 A | * | 3/1995 | Liu ...................... B01D 53/326 |
| | | | 204/252 |
| 2009/0014330 A1 | * | 1/2009 | Sugaya .............. G01N 27/4075 |
| | | | 204/424 |
| 2015/0369778 A1 | * | 12/2015 | Fujii .................... G01N 29/022 |
| | | | 506/9 |
| 2016/0077044 A1 | * | 3/2016 | Arkenberg ......... G01N 27/4074 |
| | | | 205/781 |

FOREIGN PATENT DOCUMENTS

| JP | 2011013057 A | * | 1/2011 | ........... G01N 27/406 |
| JP | 2011-069705 | | 4/2011 | |

OTHER PUBLICATIONS

Jin (J. Mater. Chem., 20, 6214-6217) (Year: 2010).*

* cited by examiner

*Primary Examiner* — J. Christopher Ball
(74) *Attorney, Agent, or Firm* — Nixon & Vanderhye, P.C.

(57) ABSTRACT

Disclosed is an ammonia sensor element having a measured gas chamber, a reference gas chamber and a solid electrolyte body arranged therebetween. The solid electrolyte body has a first main surface facing the measured gas chamber and a second main surface facing the reference gas chamber. A detection electrode is formed on the first main surface. A reference electrode is formed on the second main surface. The solid electrolyte body contains a first proton conducting solid electrolyte. The detection electrode contains a second proton conducting solid electrolyte. The second proton conducting solid electrolyte has an acid strength greater than that of the first proton conducting solid electrolyte.

8 Claims, 5 Drawing Sheets

AMMONIA SENSOR ELEMENT

CROSS-REFERENCE TO RELATED APPLICATION

This application is based on and claims the benefit of priority from Japanese Patent Application 2016-251595 filed on Dec. 26, 2016, the disclosure of which is incorporated in its entirety herein by reference.

BACKGROUND OF THE INVENTION

Technical Field of the Invention

The present disclosure relates to an ammonia sensor element which can detect ammonia in gas.

Related Art

To detect ammonia in mixed gas such as combustion gas and exhaust gas, an ammonia sensor is used. For example, a method for purifying NOx contained in exhaust gas from an internal combustion engine by using ammonia is known. To perform the purification effectively, measurement of an ammonia concentration by the use of an ammonia sensor is required. Such an ammonia sensor is required to be provided with a performance with which ammonia in exhaust gas can be detected selectively and with high accuracy.

Japanese Unexamined Patent Application Publication No. 2011-69705 (hereinafter, referred to as first published literature) discloses an ammonia sensor element comprising at least a solid electrolyte body containing a proton conducting solid electrolyte with high acidity, a measured gas-side electrode and a reference gas-side electrode. In an ammonia sensor element with such a configuration, an ammonia concentration can be measured by adsorbing ammonia in exhaust gas to the measured gas-side electrode.

SUMMARY

However, in the above-mentioned conventional ammonia sensor, the proton conducting solid electrolyte contained in the solid electrolyte body exhibits higher adsorptive properties of ammonia. Therefore, ammonia is more easily adsorbed to the solid electrolyte body than to the measured gas-side electrode. As a result, ammonia is adsorbed on the whole solid electrolyte body. Thus, there is a concern that the measured gas-side electrode cannot adsorb ammonia in gas accurately and an ammonia concentration in the gas cannot be detected accurately.

An exemplified aspect of the present disclosure is aimed at providing an ammonia sensor element which can detect, with high accuracy, an ammonia concentration in gas.

One aspect of the present disclosure is an ammonia sensor element comprising:

a measured gas chamber to which a measured gas is introduced;

a reference gas chamber to which a reference gas is introduced;

a solid electrolyte body arranged between the measured gas chamber and the reference gas chamber, having a first main surface facing the measured gas chamber and a second main surface facing the reference gas chamber;

a detection electrode formed on the first main surface of the solid electrolyte body; and a reference electrode formed on the second main surface of the solid electrolyte body, wherein the solid electrolyte body contains a first proton conducting solid electrolyte, the detection electrode contains a second proton conducting solid electrolyte, and the second proton conducting solid electrolyte has an acid strength greater than that of the first proton conducting solid electrolyte.

Other aspects of the present disclosure will be apparent from the descriptions of the embodiments on the basis of the drawings described below.

DETAILED DESCRIPTION OF THE PREFERRED EMBODIMENTS

First Embodiment

Figure 1:
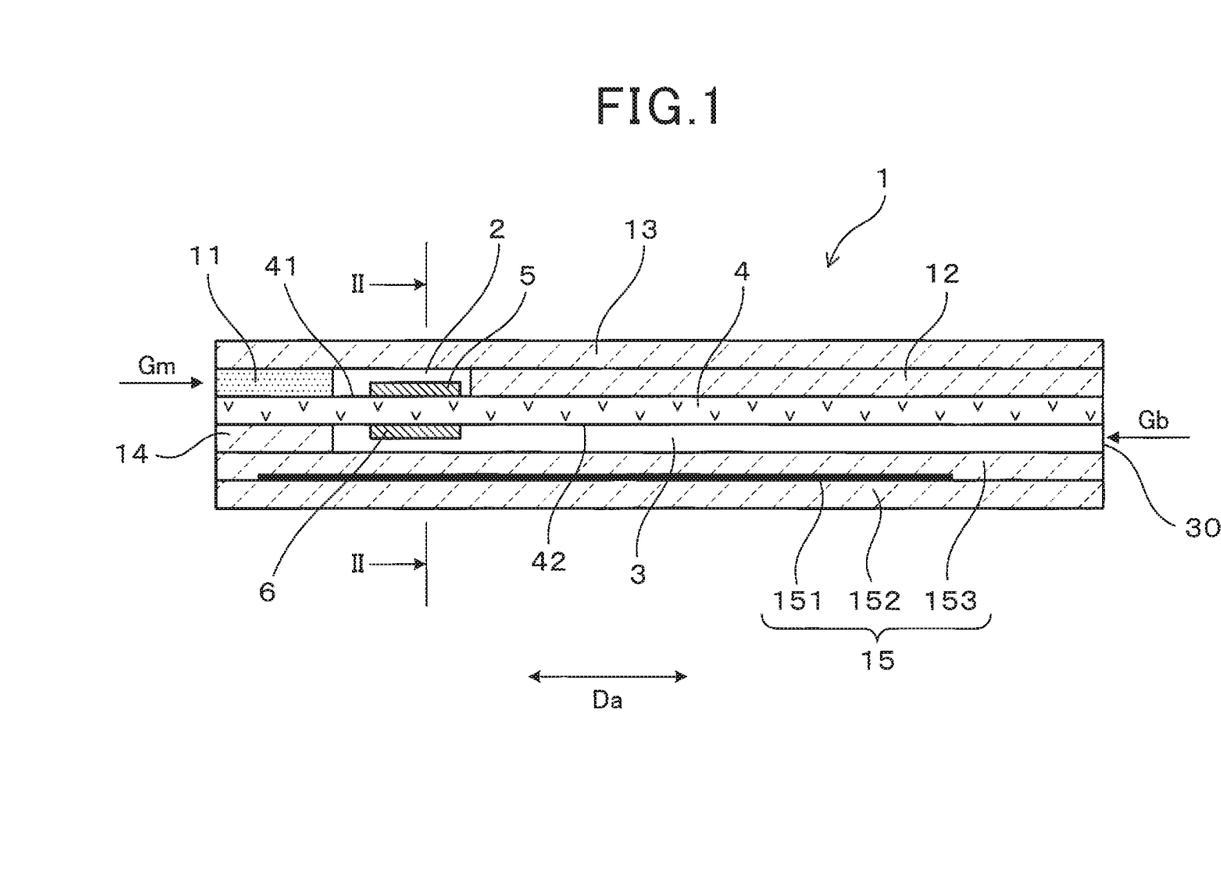
FIG. 1 shows a longitudinal cross-sectional view of an ammonia sensor element in the first embodiment.

The embodiment of an ammonia sensor element is described with reference to FIGS. 1-3. As exemplified in FIG. 1 and FIG. 2, an ammonia sensor element 1 includes a measured gas chamber 2, a reference gas chamber 3, a solid electrolyte body 4, a detection electrode 5 and a reference electrode 6. The shape of the ammonia sensor element 1 is not particularly limited, but is, for example, an elongated-plate shape as exemplified in FIG. 1. In the present description, one end of both ends of the ammonia sensor element 1 in an elongated direction Da to be exposed to measured gas is referred to as a distal end, and the opposite end is referred to as a proximal end. In some cases, the elongated direction is referred to as an axial direction. In FIG. 1, the left side is a distal-end side in the axial direction Da, and the right side is a proximal-end side in the axial direction Da.

The measured gas chamber 2 is a space to which measured gas Gm is introduced. The measured gas Gm is a mixed gas which may contain ammonia, for example such as exhaust gas. If the measured gas Gm is exhaust gas, the measured gas Gm contains oxygen, nitrogen, carbon dioxide, nitrogen oxide, ammonia, hydrogen, hydrocarbon, water and the like. The measured gas chamber 2 is a space surrounded by the solid electrolyte body 4, a diffusion layer 11, a first spacer 12 and an insulator 13.

The diffusion layer 11, the first spacer 12 and the insulator 13 are formed of an electrically-insulating ceramic such as for example alumina. The diffusion layer 11 is formed of a gas-permeable porous body with high porosity. The measured gas Gm passing through the diffusion layer 11 is introduced into the measured gas chamber 2. That is, the measured gas chamber 2 opens to the outside via the diffusion layer 11. The first spacer 12 and the insulator 13 are formed of a dense body through which gas does not substantially penetrate. Preferably, the first spacer 12 and the insulator 13 are integrally sintered.

The reference gas chamber 3 is a space to which reference gas Gb is introduced. The reference gas Gb is for example atmospheric air. The reference gas chamber 3 is a space surrounded by the solid electrolyte body 4, a second spacer 14 and a ceramic heater 15. The second spacer 14 is formed of a dense body through which gas does not substantially penetrate. Furthermore, the ceramic heater 15 has a heat-generating unit 151 inside, and the surrounding of the heat-generating unit 151 is formed of a dense body through which gas does not substantially penetrate.

As exemplified in FIG. 1, the reference gas chamber 3 has an opening 30, for example, on the base-end side in the axial direction Da, and the reference gas Gb is introduced from the opening 30. In the measured gas chamber 2, the above-mentioned diffusion layer 11 serves as an introduction port of the measured gas Gm. A position to form the diffusion layer 11 is not particularly limited, but is for example a distal end in the axial direction Da as exemplified in FIG. 1. The diffusion layer 11 can be formed also on the side surface orthogonal to the axial direction Da as far as it exists on the distal-end side in the axial direction Da.

The solid electrolyte body 4 is arranged between the measured gas chamber 2 and the reference gas chamber 3. The solid electrolyte body 4 contains a first proton conducting solid electrolyte 45. Hereinafter, the first proton conducting solid electrolyte is referred to as a "first solid electrolyte" as appropriate. Preferably, the first solid electrolyte 45 is made of perovskite-type oxide. In this case, the solid electrolyte body 4 exhibits excellent protonic conductivity, therefore, the sensitivity of the ammonia sensor element 1 is improved.

Examples of perovskite-type oxides include, but are not particularly limited to, strontium zirconate, calcium zirconate, barium zirconate, strontium cerate, calcium cerate, barium cerate and the like, doped with rare-earth elements such as Y and Yb. The solid electrolyte body can contain at least one kind of perovskite-type oxide among them. In terms of expansion of a detection temperature range of the ammonia sensor element 1, barium zirconate and strontium zirconate are preferable among them, and barium zirconate and strontium zirconate doped with rare-earth elements are more preferable.

The solid electrolyte body 4 has a first main surface 41 and a second main surface 42. The first main surface faces the measured gas chamber 2. On the first main surface 41, the detection electrode 5 is formed. The detection electrode 5 is in contact with the solid electrolyte body 4 at the first main surface 41. On the second main surface 42, the reference electrode 6 is formed. The reference electrode 6 is in contact with the solid electrolyte body 4 at the second main surface 42. That is, in the gas sensor element 1, the reference electrode 6, the solid electrolyte body 4 and the detection electrode 5 are laminated in this order.

Figure 3:
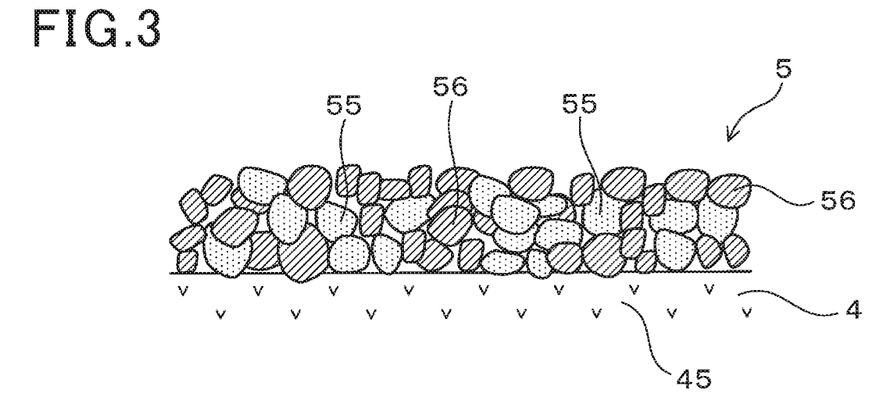
FIG. 3 shows an enlarged cross-sectional view of an interface between a detection electrode containing a second solid electrolyte and a solid electrolyte body in the first embodiment.

As exemplified in FIG. 3, the detection electrode 5 contains a second proton conducting solid electrolyte 55. Hereinafter, the second proton conducting solid electrolyte is referred to as a "second solid electrolyte" as appropriate. The second solid electrolyte 55 is a proton conducting solid electrolyte having an acid strength greater than that of the first solid electrolyte 45 in the solid electrolyte body 4. Therefore, the second solid electrolyte can be referred to also as an acidic solid electrolyte. The acid strength has the same meaning as the ammonia adsorption strength in the experimental example 1 stated below. Therefore, the acid strengths of the first solid electrolyte 45 and the second solid electrolyte 55 can be compared by measuring the ammonia adsorption strengths thereof. It is considered that the higher the ammonia adsorption strength is, the greater the acid strength is.

The second solid electrolyte 55 is preferably an acidic proton conducting solid electrolyte. In this case, the second solid electrolyte 55 more easily adsorbs basic ammonia. That is, the detection electrode 5 containing the second solid electrolyte 55 more easily adsorbs ammonia. Thus, detection accuracy of the ammonia sensor element 1 is improved. In terms of improving further detection accuracy, the second solid electrolyte 55 is more preferably made of a phosphoric acid-based compound.

The phosphoric acid-based compound includes phosphate, pyrophosphate and the like. An element to be paired includes lanthanum, tin, zirconium, calcium, cerium, silicon, aluminum, titanium and the like. Specifically, as the phosphoric acid-based compound, exemplified are lanthanum phosphate, lanthanum pyrophosphate, tin phosphate, tin pyrophosphate, zirconium phosphate, zirconium pyrophosphate, calcium phosphate, calcium pyrophosphate, cerium phosphate, cerium pyrophosphate, silicon phosphate, silicon pyrophosphate, aluminum phosphate, aluminum pyrophosphate, titanium phosphate, titanium pyrophosphate, tungsten phosphate, apatite and the like. The detection electrode 5 can contain, as the second solid electrolyte 55, at least one kind of transition metal phosphorous compound among them.

Among them, the phosphoric acid-based compound is preferably at least one kind selected from a group consisting of lanthanum phosphate, tin phosphate, tin pyrophosphate, zirconium phosphate and zirconium pyrophosphate. In this case, the second solid electrolyte 55 more easily adsorbs basic ammonia, and thus, the detection electrode 5 more easily adsorbs ammonia. As a result, detection accuracy of the ammonia sensor element 1 is further improved.

As exemplified in FIG. 3, the detection electrode 5 can contain the above-mentioned second solid electrolyte 55, and further, a metal 56. Preferably, the metal 56 in the detection electrode 5 has excellent conductivity. As the metal 56, exemplified are precious metals such as Pt, Ag, Au, Pd, Ru, and Rh, Ni, Al, Cu, W and the like.

Preferably, it is preferable that the metal 56 contains at least Pt. In this case, Pt can catalyze the combustion of reducing gas such as hydrogen, thereby improving further selective decomposition activity of ammonia of the detection electrode 5. Therefore, detection accuracy of the ammonia sensor element 1 is further improved.

The blending ratio between the second solid electrolyte 55 and the metal 56 in the detection electrode 5 can be adjusted as appropriate. The content of the second solid electrolyte in the detection electrode can be adjusted in the range of 3-100 parts by mass relative to 100 parts by mass of the metal. The content of the metal in the detection electrode 5 can be within, for example, 50-97 mass %.

As exemplified in FIG. 3, the detection electrode 5 preferably has a structure in which the second solid electrolyte 55 and the metal 56 are mutually three dimensionally intermixed. That is, preferably, a phase made of the second solid electrolyte 55 and a phase made of the metal 56 are mutually mixed three dimensionally. In this case, reaction points in the detection electrode 5 are increased. The reaction point is a three-phase interface of gas phase ammonia, the second solid electrolyte 55 and the metal 56. Therefore, a decomposition activity of ammonia in the detection electrode 5 is improved. This can decrease reaction resistance of the electrode. As a result, a temperature range in which ammonia can be decomposed can be expanded. In this regard, the detection electrode 5 preferably forms a continuous phase by having mutually connected phases of the second solid electrolyte in a matrix of the metal.

Figure 4:
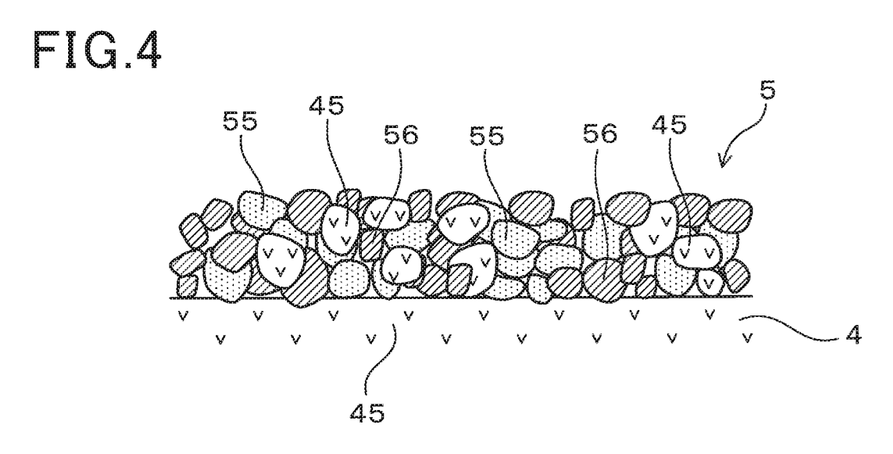
FIG. 4 shows an enlarged cross-sectional view of an interface between a detection electrode containing a first solid electrolyte and a second solid electrolyte and a solid electrolyte body in the first embodiment.

The detection electrode 5 can further contain perovskite-type oxide. In this case, the detection electrode 5 exhibits a decomposition activity of ammonia also at a three-phase interface of ammonia, perovskite-type oxide and metal. Since the perovskite-type oxide exhibits excellent protonic conductivity, in this case, an ammonia decomposition activity of the detection electrode 5 can be further improved. As a result, reaction resistance of the detection electrode 5 is more decreased and an ammonia decomposable temperature range in the ammonia sensor element 1 can be expanded. As the perovskite-type oxide in the detection electrode 5, those similar to the above-mentioned first solid electrolyte 45 are exemplified. FIG. 4 shows an example in which the detection electrode 5 contains, as perovskite-type oxide, the first solid electrolyte 45. As exemplified in FIG. 4, the detection electrode 5 can contain the first solid electrolyte 45, the second solid electrolyte 55 and the metal 56. When the detection electrode 5 contains, as perovskite-type oxide, the first solid electrolyte 45 similarly in the solid electrolyte body 4, adhesiveness between the detection electrode 5 and the solid electrolyte body 4 can be improved. Perovskite-type oxide in the detection electrode 5 may be the same type as in the solid electrolyte body 4 as described above, however may be a different type. When the detection electrode 5 contains perovskite-type oxide, the content of perovskite-type oxide can be in the range of 3-100 parts by mass relative to 100 parts by mass of metal. The content of the second solid electrolyte can be adjusted in the range of 10-100 parts by mass relative to 100 parts by mass of perovskite-type oxide, and preferably is equal to or less than 50 parts by mass, and more preferably, is equal to or less than 30 parts by mass. In this case, an ammonia decomposition activity of the detection electrode 5 can be further improved while selective adsorptive properties for ammonia are sufficiently exerted.

The solid electrolyte body 4 can further contain a proton conducting solid electrolyte made of a phosphoric acid-based compound, but preferably, does not substantially contain a phosphoric acid-based compound. That is, it is preferable that the content of phosphoric acid-based compound in the solid electrolyte body 4 is substantially 0. In this case, adsorption of ammonia to the solid electrolyte body 4 is suppressed, and ammonia is more easily adsorbed to the detection electrode 5. Therefore, an ammonia concentration can be detected more accurately. Furthermore in this case, increase in proton conduction resistance at the interface between dissimilar materials, the solid electrolyte body 4 and the phosphoric acid-based compound, can be suppressed. Therefore, the solid electrolyte body 4 exhibits good protonic conductivity, allowing further expansion of an ammonia decomposable temperature range.

The reference electrode 6 is formed of, for example, a metal having excellent conductivity. Examples of such metal include a similar metal to the metal 56 of the detection electrode 5 mentioned above. The reference electrode 6 can contain the above-mentioned first proton conducting solid electrolyte with the metal. Specifically, the reference electrode 6 can contain the metal and perovskite-type oxide. Perovskite-type oxide may be the same type or a different type of that in the solid electrolyte body 4. In terms of increase in adhesiveness between the solid electrolyte body 4 and the reference electrode 6, the same type is preferable. The blending ratio between the first proton conducting solid electrolyte and the metal in the reference electrode 6 can be adjusted as appropriate. The blending ratio of the first proton conducting solid electrolyte such as perovskite-type oxide to the total amount 100 parts by mass of the first proton conducting solid electrolyte and the metal can be adjusted in the range of, for example, 3-50 parts by mass.

The second spacer 14 and the ceramic heater 15 forming the reference gas chamber 3 are formed of electric-insulating ceramic such as alumina. Furthermore, the ceramic heater 15 has a heat-generating unit 151 inside, and this heat-generating unit 151 is sandwiched by a first insulation layer 152 and a second insulation layer 153. The first insulation layer 152 and the second insulation layer 153 are made of, for example, a dense body of alumina.

The thickness of the detection electrode 5 can be formed, for example, in the range of 5-100 μm. Also, the thickness of the reference electrode 6 can be formed, for example, in the range of 5-100 μm similarly.

The ammonia sensor element 1 is obtained by, for example, laminating and sintering various ceramic sheets for forming the solid electrolyte body 4, the first spacer 12, the insulator 13, the second spacer 14 and the heater 15. Before lamination, various electrode pastes for forming the detection electrode 5 and the reference electrode 6 are applied to the ceramic sheet for forming the solid electrolyte body 4. Furthermore, an electrode paste for forming the heat-generating unit 151, various leads to apply a voltage to the heat-generating unit 151 and the like are applied to the ceramic sheet for forming the first insulation layer 152 or the second insulation layer 153 of the heater 15.

A detection electrode paste (electrode paste for forming the detection electrode 5) is obtained by mixing a metal powder such as Pt powder, the second solid electrolyte and an organic binder and kneading them sufficiently. A reference electrode paste (electrode paste for forming the reference electrode 6) is obtained by mixing a metal powder such as Pt powder, the first proton conducting solid electrolyte and an organic binder and kneading them sufficiently. The electrode paste for forming the heat-generating unit 151 and various leads is obtained by, for example, mixing a metal powder such as Pt powder and an organic binder and kneading them sufficiently.

Figure 2:
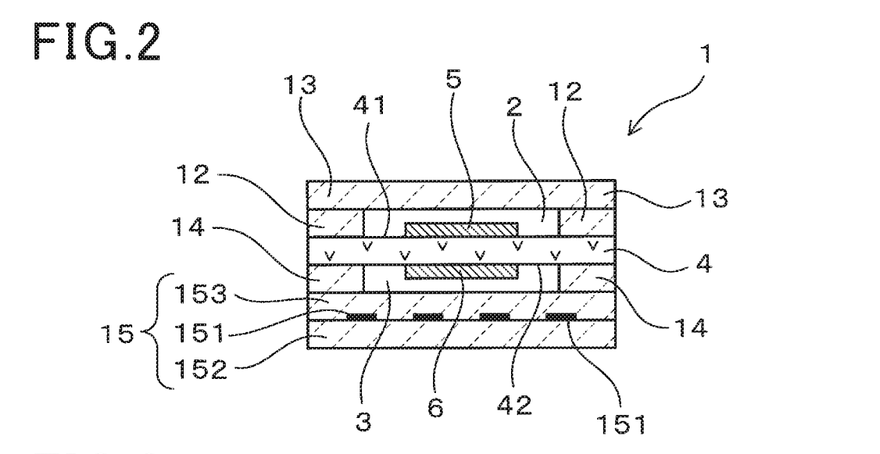
FIG. 2 shows a cross-sectional view taken across the line II-II of FIG. 1.

In the ammonia sensor element 1 exemplified in FIGS. 1-3, measured gas Gm is introduced to the measured gas chamber 2 through the diffusion layer 11 from the outside of the ammonia sensor element 1. Ammonia in the measured gas Gm is decomposed according to the following reaction formula (I) in the detection electrode 5 facing the measured gas chamber 2, to produce protons.

$$2NH_3 \rightarrow N_2 + 6H^+ + 6e^- \tag{I}$$

Protons produced in the detection electrode 5 are conducted through the solid electrolyte body 4 to the reference electrode 6, and water is produced according to the following reaction formula (II) in the reference electrode 6.

$$6H^+ + 3/2O_2 + 6e^- \rightarrow 3H_2O \tag{II}$$

In the detection electrode 5 and the reference electrode 6, when reactions of the above-mentioned formula (I) and formula (II) proceed smoothly, diffusion of ammonia to the detection electrode 5 is a rate-controlling reaction. This is because ammonia supply is restricted by the diffusion layer 11. Thus, a limiting current depending on an ammonia concentration is observed between the detection electrode 5 and the reference electrode 6. The ammonia sensor element 1 can detect an ammonia concentration on the basis of this limiting current.

As exemplified in FIGS. 1-3, the ammonia sensor element 1 of the present embodiment contains, in the solid electrolyte body 4 and the detection electrode 5, proton conducting solid electrolytes with respectively different acid strengths. The detection electrode 5 contains the second solid electrolyte 55 having the acid strength greater than that of the first solid electrolyte 45 in the solid electrolyte body 4. Therefore, basic ammonia contained in the measured gas Gm is easily adsorbed selectively to the detection electrode 5. As a result, ammonia is selectively decomposed in the detection electrode 5, and the ammonia sensor element 1 can detect an ammonia concentration in the measured gas Gm with high accuracy. The ammonia sensor element 1 can detect selectively basic ammonia from the measured gas of, for example, mixed gas with high accuracy.

The ammonia sensor element 1 can be used for detecting ammonia in various mixed gases. Thus, the ammonia sensor element 1 has, on the outer surface, a contact with mixed gas. The concept of this contact includes not only a part actually in contact with gas but also a part to be in contact with gas.

Preferably, the ammonia sensor element 1 is used for detecting an ammonia concentration in exhaust gas discharged from an internal combustion engine of an automobile and the like. Thus, the ammonia sensor element 1 preferably has contact with exhaust gas. In this case, detection accuracy of an ammonia concentration is further improved. This is because ammonia is substantially the only basic gas contained in exhaust gas, thereby causing adsorption of basic gas other than ammonia to be substantially absent. A contact with exhaust gas in the ammonia sensor element 1 of the present embodiment is, for example, a distal end in the axial direction.

As above, the ammonia sensor element 1 of the present embodiment can detect an ammonia concentration in gas such as exhaust gas with high accuracy.

Experimental Example 1

The present example is an example for comparing/evaluating an adsorption strength of ammonia and electrode reaction resistance of a detection electrode. First, two kinds of samples were prepared to measure an adsorption strength of ammonia. One of them was a sample E1 and the other was a sample C1.

The sample E1 was a mixed powder of Pt powder and a powder of second solid electrolyte. Lanthanum phosphate powder was used as the powder of second solid electrolyte. The blending ratio between Pt powder and lanthanum phosphate powder was Pt:lanthanum phosphate=7:3 in the mass ratio. The sample C2 was Pt powder.

[Measurement of Adsorption Strength of Ammonia]

Measurement was carried out as below. First, each of the samples was filled in a sample tube. Then, the temperature within the sample tube was raised to 800° C. at a temperature-rising speed of 10° C./min while He gas was distributed within the sample tube, and subsequently the sample was naturally cooled. This removed moisture and gas attached to the sample.

Then, basic gas was distributed within the sample tube for 15 minutes at a temperature of 50° C. $NH_3$ gas in He balance was used as the basic gas. This produced $NH_3$ adsorption onto the sample. Then, the supply of $NH_3$ gas was stopped, and the temperature within the sample tube was raised to 800° C. at a temperature-rising speed of 10° C./min with He gas being distributed. $NH_3$ desorbed from the sample at this time was detected by a mass analyzer attached downstream of the sample tube, to determine the quantity of $NH_3$ desorbed from the sample. The result is shown in FIG. 5.

By using, as the sample, the above-mentioned first solid electrolyte and second solid electrolyte, acid strengths thereof can be measured. In this case, the greater quantity of $NH_3$ desorbed from the sample means that the greater quantity of $NH_3$ had been adsorbed to the sample, and the acid strength is considered to be greater.

Figure 5:
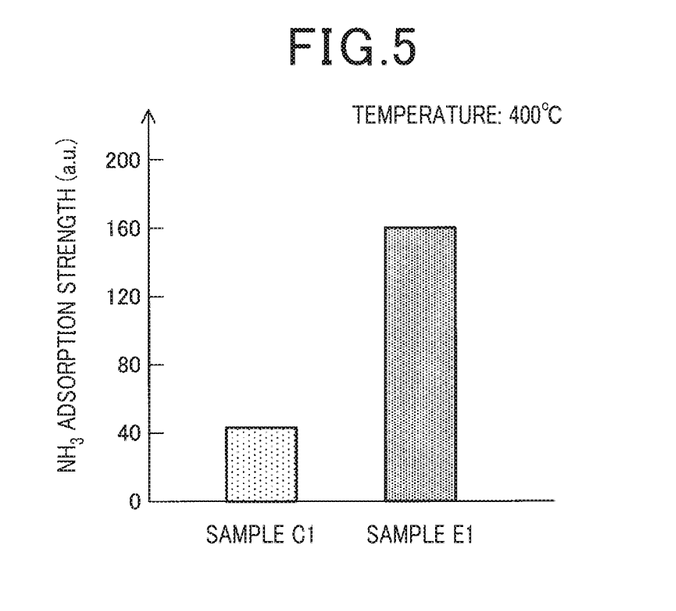
FIG. 5 is a graph showing ammonia adsorption strengths of sample E1 and sample C1 respectively in the first experimental example.

As known from FIG. 5, the sample E1 has an acid strength greater than that of the sample C1. That is, the sample E1 has a greater adsorption strength of ammonia. This means that the detection electrode of the first embodiment containing the second solid electrolyte as the sample E1 has a greater adsorption strength of ammonia.

Furthermore, two kinds of samples were prepared to measure electrode reaction resistance. One of them was referred to as a sample E2, and the other was referred to as a sample C2.

The sample E2 was prepared as follows. First, a disc-like solid electrolyte body having a diameter of 12 mm and the thickness of 1 mm was prepared. This solid electrolyte body was obtained by sintering a pellet-like proton conducting solid electrolyte. The solid electrolyte body contained, as the proton conducting solid electrolyte, strontium zirconate doped with Yb. The strontium zirconate doped with Yb is hereinafter referred to as "YbSZ" as appropriate. Then, Pt powder, a powder of the second solid electrolyte and an organic binder were mixed and sufficiently kneaded, to prepare an electrode paste for the detection electrode. Lanthanum phosphate powder was used as the powder of second solid electrolyte. The blending ratio between Pt powder and lanthanum phosphate powder was Pt:lanthanum phosphate in the mass ratio of 7:3. Furthermore, Pt powder and an organic binder were mixed and sufficiently kneaded, to prepare an electrode paste for reference electrode.

Then, the electrode paste for the detection electrode was printed on one surface of the disc-like solid electrolyte body, and was dried at a temperature of 70° C., thereby forming a disc-like detection electrode printing layer having a diameter of 10 mm. Furthermore, the electrode paste for reference electrode was printed on the other plane of the solid electrolyte body, and was dried, thereby forming a disc-like reference electrode printing layer having a diameter of 10 mm. Then each of the printing layers was fired at a temperature of 1200° C., thereby preparing a cell with a structure in which the disc-like solid electrolyte body was sandwiched between the detection electrode and the reference electrode. This cell was the sample E2.

Furthermore, the electrode paste for reference electrode was printed on both planes of the disc-like solid electrolyte body, and similar processes to those for the sample E2 were performed, to prepare a cell. This cell was the sample C2.

[Measurement of Electrode Reaction Resistance]

Measurement was carried out as below using the sample E2 and the sample C2 prepared as above. First, a current collector and a lead wire were attached respectively to the detection electrode and the reference electrode in each of the samples. Then, each of the samples was placed inside an electric tube furnace. Then, the temperature within the electric tube furnace was raised to 400° C. while $NH_3$ gas in $N_2$ balance was distributed within the electric tube furnace. The lead and an impedance analyzer were connected, and cell resistance was separated into ohmic resistance and electrode reaction resistance by an alternate-current impedance method. The result of electrode reaction resistance is shown in FIG. 6.

Figure 6:
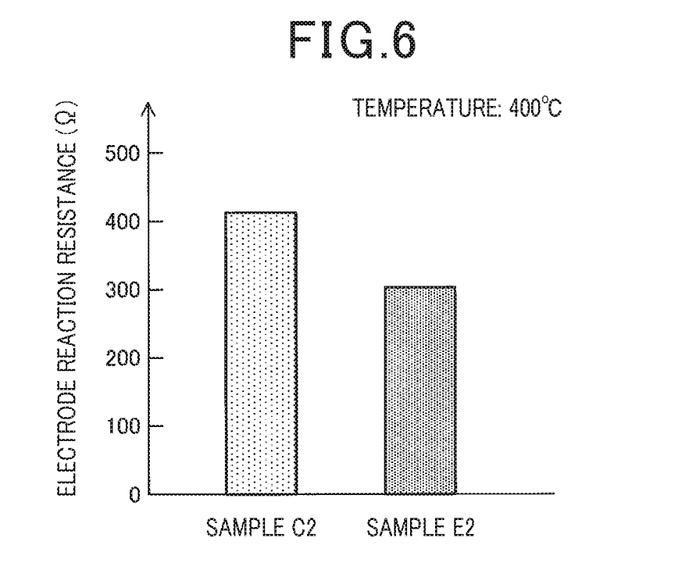
FIG. 6 is a graph showing electrode reaction resistances of sample E2 and sample C2 respectively in the first experimental example.

As can be seen from FIG. 6, the sample E2 has electrode reaction resistance lower than that of the sample C2. That is, the sample E2 has higher decomposition activity of ammonia. This means that the ammonia sensor element 1 of the first embodiment having a detection electrode containing the second solid electrolyte such as the sample E2 has excellent sensitivity to ammonia. Also this means that a decomposable temperature range of ammonia is wider.

Thus, according to the present experimental example, it would be known that the ammonia sensor element having the detection electrode containing the second solid electrolyte can detect ammonia with high accuracy and sensitivity.

Embodiment 2

The present embodiment is an example of detection electrode having at least two-layer structure. Meanwhile, unless otherwise indicated, the same numerals used in the second and succeeding embodiments as those used in the previous embodiment represent analogous components and the like to those in the previous embodiment.

Figure 7:
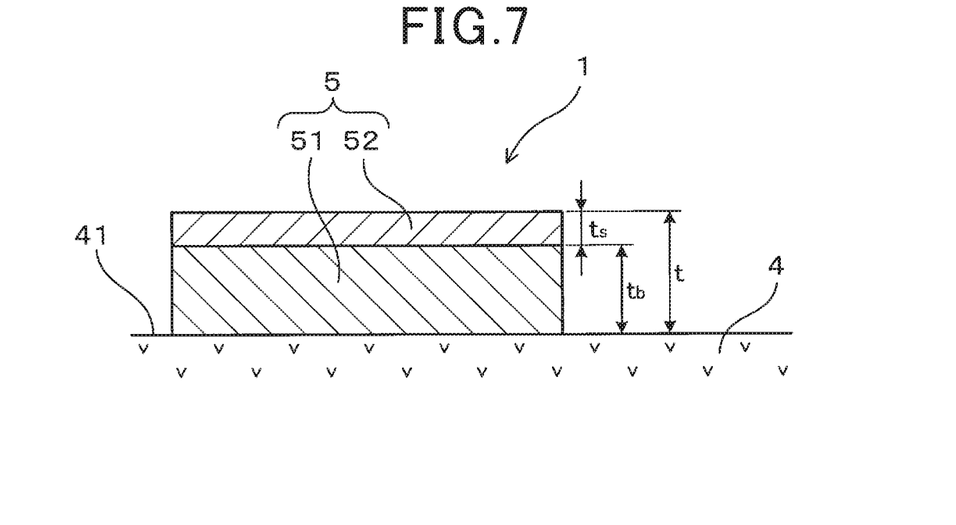
FIG. 7 shows a cross-sectional view of a detection electrode of an ammonia sensor element in the second embodiment.

In an ammonia sensor element 1 of the present embodiment, a detection electrode 5 has an electrode base layer 51 and an electrode surface layer 52 formed thereon as exemplified in FIG. 7. Specifically, the electrode base layer 51 is formed on a first main surface 41 of a solid electrolyte body 4. The solid electrolyte body 4 and the electrode base layer 51 are in contact with each other. The electrode surface layer 52 is formed on the electrode base layer 51. The electrode base layer 51 and the electrode surface layer 52 are in contact with each other. That is, the solid electrolyte body 4, the electrode base layer 51 and the electrode surface layer 52 are laminated in this order. The electrode base layer 51 and the electrode surface layer 52 form the detection electrode 5.

Figure 8:
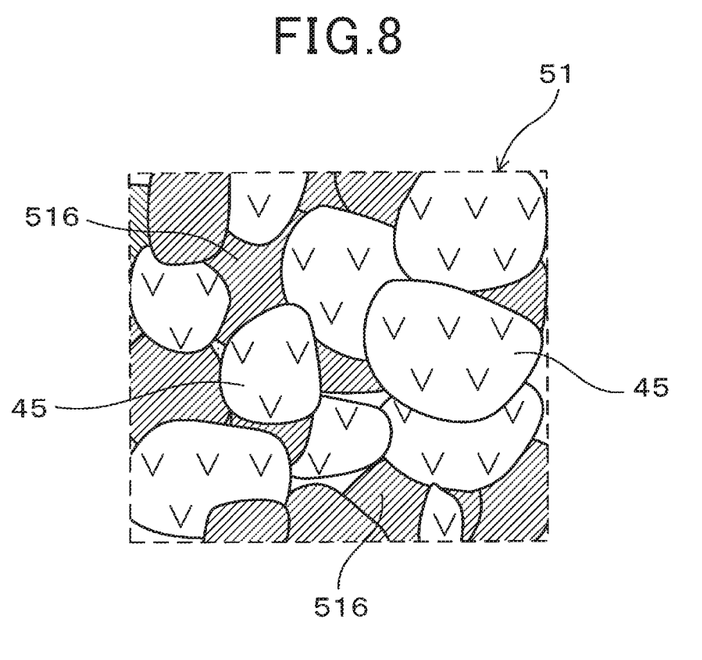
FIG. 8 shows an enlarged cross-sectional view of an electrode base layer in the second embodiment.

As exemplified in FIG. 8, the electrode base layer 51 contains a metal 516 and a first solid electrolyte 45. Examples of the metal 516 include precious metals such as Pt, Ag, Au, Pd, Ru, and Rh, Ni, Al, Cu, W and the like similarly to the first embodiment, and preferably it is better to contain at least Pt. The first solid electrolyte 45 is similar to that in the solid electrolyte body 4 in the first embodiment, and is preferably perovskite-type oxide.

The blending ratio between the first solid electrolyte 45 and the metal 516 in the electrode base layer 51 can be adjusted as appropriate. In the electrode base layer 51, a blending amount of the first solid electrolyte 45 relative to the total amount 100 parts by mass of the first solid electrolyte 45 and the metal 516 can be adjusted in the range of, for example, 3-50 parts by mass.

Figure 9:
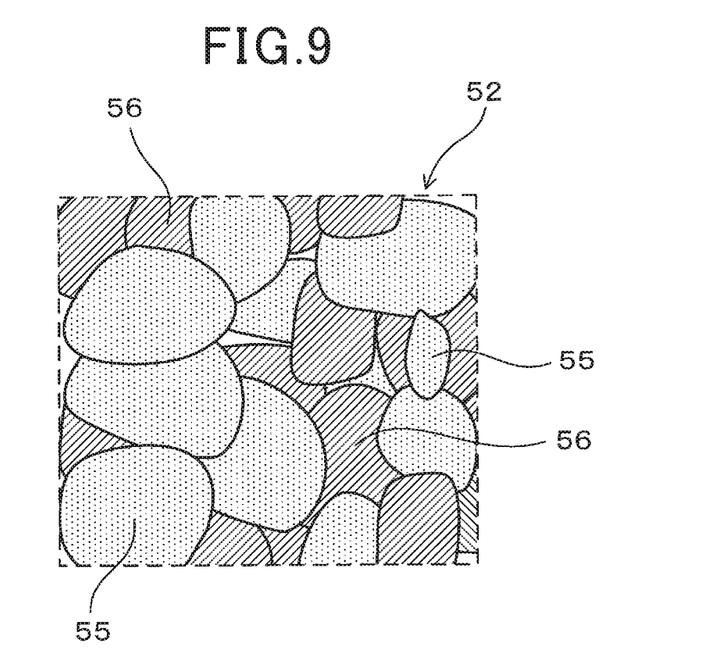
FIG. 9 shows an enlarged cross-sectional view of an electrode surface layer in the second embodiment.

As exemplified in FIG. 9, the electrode surface layer 52 contains the metal 56 and a second solid electrolyte 55. Within the electrode surface layer 52, the metal 56 and the second solid electrolyte 55 are mixed up. The electrode surface layer 52 can contain further perovskite-type oxide. That is, the electrode surface layer 52 can form a similar configuration to that of the detection electrode 5 in the first embodiment.

The detection electrode 5 having the electrode base layer 51 and the electrode surface layer 52 is formed for example as follows. First, a metal powder such as Pt powder, the first solid electrolyte and an organic binder are mixed, and sufficiently kneaded, thereby preparing an electrode paste for electrode base layer 51. Furthermore, a metal powder such as Pt powder, the second solid electrolyte and an organic binder are mixed, and are sufficiently kneaded, thereby preparing an electrode paste for electrode surface layer 52.

Then, the electrode paste for electrode base layer 51 is printed on a ceramic sheet for solid electrolyte body 4 and is dried. Then, the electrode paste for electrode surface layer 52 is printed on a printing part of the electrode paste for electrode base layer 51 and is dried. Subsequently, firing is carried out, allowing to form the detection electrode 5 having the electrode base layer 51 and the electrode surface layer 52 on the solid electrolyte body 4.

An action effect of the ammonia sensor element 1 of the present embodiment is now described. In the ammonia sensor element 1 of the present embodiment, the detection electrode 5 has a two-layer structure of the electrode base layer 51 and the electrode surface layer 52. The electrode surface layer 52 contains, as a proton conducting solid electrolyte, the second solid electrolyte having greater acid strength made of, for example, a phosphoric acid-based compound. Therefore, in the detection electrode 5, the electrode surface layer 52 can selectively adsorb ammonia. Then, ammonia is decomposed in, for example, the electrode surface layer 52, to produce protons as above.

This proton is conducted through the electrode base layer 51 containing the first solid electrolyte excellent in protonic conductivity made of, for example, perovskite-type oxide, to the solid electrolyte body 4. Therefore, in the ammonia sensor element 1 of the present embodiment, ammonia adsorption, decomposition and proton conduction rapidly occur, and electrode reaction resistance can be further decreased, thereby allowing further improvement in detection accuracy and sensitivity to ammonia of the ammonia sensor element 1.

As exemplified in FIG. 8, the electrode base layer 51 preferably has the structure in which the first solid electrolyte 45 and the metal 516 are mutually three dimensionally intermixed. That is, it is preferable that a phase of the first solid electrolyte 45 and a phase of the metal 516 are mutually mixed up three dimensionally. In this case, reaction points in the electrode base layer 51 are increased, and electrode reaction resistance can be further decreased.

As exemplified in FIG. 7, the thickness t of the detection electrode 5, the thickness $t_b$ of the electrode base layer 51 and the thickness $t_s$ of the electrode surface layer 52 preferably fulfill the relations of the following formula (1) and the following formula (2). In this case, electrode reaction resistance of the ammonia sensor element 1 can be further improved. This improvement effect will be described in detail in experimental example 2 stated below.

$$t=t_b+t_s \quad (1)$$

$$0.1<t_s/t_b<1 \quad (2)$$

In the ammonia sensor element 1 of the present embodiment, other configurations are similar to those of the first embodiment. Also in the present embodiment, an action effect similar to that of the first embodiment can be obtained.

Experimental Example 2

The present example is an example for evaluating, in a detection electrode with two-layer structure in the second embodiment, the relation between the thickness ratio of the electrode base layer and the electrode surface layer and electrode reaction resistance. First, a sample for evaluation was prepared as below.

Specifically, first, a disc-like solid electrolyte body having a diameter of 12 mm and the thickness of 1 mm was prepared. This solid electrolyte body was similar to that of the experimental example 1.

Then, Pt powder, a powder of first solid electrolyte and an organic binder were mixed, and sufficiently kneaded, to prepare an electrode paste for electrode base layer. YbSZ powder was used as the powder of first solid electrolyte. The blending ratio between Pt powder and YbSZ powder was Pt:YbSZ=7:3 in the mass ratio.

Furthermore, Pt powder, a powder of second solid electrolyte and an organic binder were mixed, and sufficiently kneaded, to prepare an electrode paste for electrode surface layer. This electrode paste was similar to the electrode paste for the detection electrode in the experimental example 1. Furthermore, Pt powder and an organic binder were mixed and sufficiently kneaded, to prepare an electrode paste for reference electrode similar to that in the experimental example 1.

Then, the electrode paste for electrode base layer was printed on one plane of the disc-like solid electrolyte body and subsequently was dried, thereby forming a disc-like printing layer for electrode base layer having a diameter of 10 mm. Then, on this printing layer, the electrode paste for electrode surface layer was laminated/printed, and was dried, thereby laminating/forming a disc-like printing layer for electrode surface layer having a diameter of 10 mm.

The electrode paste for reference electrode was printed on the other plane of the solid electrolyte body and was dried, thereby forming a disc-like printing layer for reference electrode having a diameter of 10 mm. Subsequently, each of the printing layers was fired at a temperature of 1200° C. Thus, prepared was a cell with a structure in which the disc-like solid electrolyte body was sandwiched between the detection electrode having the electrode base layer and the electrode surface layer and the reference electrode. This cell was a sample for evaluation in the present example.

Figure 10:
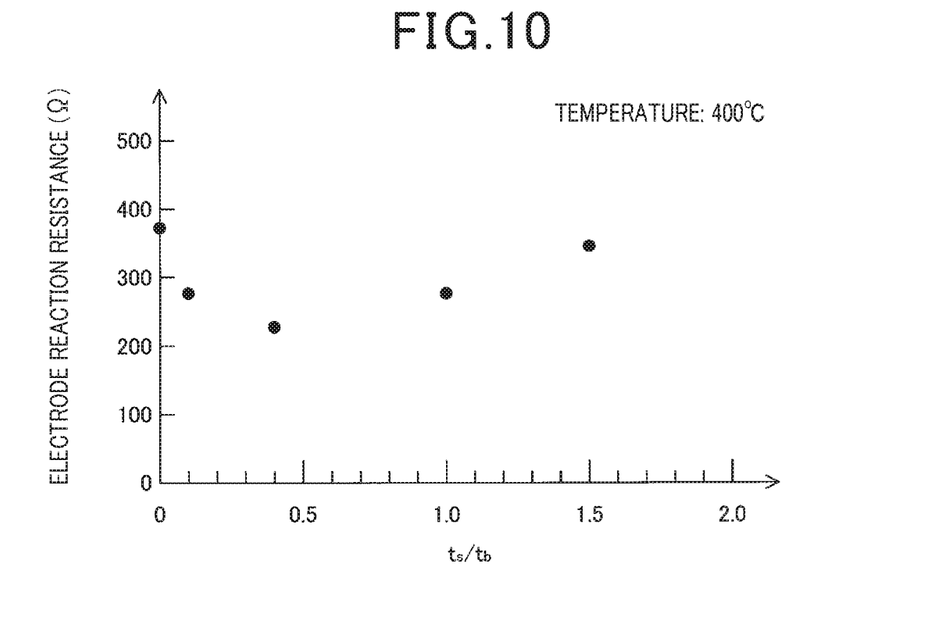
FIG. 10 is a graph showing the relation between the ratio $t_s/t_b$, $t_b$ being the thickness of an electrode base layer of a detection electrode and $t_s$ being the thickness of an electrode surface layer thereof, and electrode reaction resistance in the second experimental example.

In the present example, multiple samples were prepared by changing the thickness ratio between the printing layer for electrode base layer and the printing layer of electrode surface layer. With regard to each of the samples, electrode reaction resistance was measured similarly to the experimental example 1. The result thereof is shown in FIG. 10. In FIG. 10, the horizontal axis represents the ratio $t_s/t_b$, $t_s$ being the thickness of the electrode surface layer and $t_b$ being the thickness of the electrode base layer, and the vertical axis represents electrode reaction resistance.

As known from FIG. 10, forming the electrode surface layer on the electrode base layer allows decrease in electrode reaction resistance. On the other hand, when the thickness ratio $t_s/t_b$ exceeds a predetermined value, electrode reaction resistance turns upward from the decrease. In terms of sufficient decrease in electrode reaction resistance, it is preferable that $t_b/t_s$ is 0.1 to 1. In terms of further decrease in electrode reaction resistance, $t_b/t_s$ is more preferably 0.2 to 0.8, and further preferably is 0.3 to 0.6.

As described above, according to the present disclosure, the above ammonia sensor element contains, in a solid electrolyte body and a detection electrode, proton conducting solid electrolytes respectively with different acid strengths. The detection electrode contains a second proton conducting solid electrolyte with the acid strength greater than that of a first proton conducting solid electrolyte contained in the solid electrolyte body. Therefore, ammonia is easily adsorbed to the detection electrode. In other words, the second proton conducting solid electrolyte with greater acid strength easily adsorbs basic ammonia selectively, and ammonia is selectively adsorbed to the detection electrode containing such second proton conducting solid electrolyte. As a result, ammonia is selectively decomposed in the detection electrode. Therefore, the ammonia sensor element can detect an ammonia concentration with high accuracy.

A proton conducting solid electrolyte responds to $H^+$, therefore, there is a concern that an ammonia sensor using a proton conducting solid electrolyte generally responds not only to ammonia but also to $H_2O$, hydrocarbon (HC) and the like. In an ammonia sensor element of the above aspect, a detection electrode contains a second proton conducting solid electrolyte, and therefore, basic ammonia from, for example, mixed gas can be selectively adsorbed to the detection electrode. Therefore, detection accuracy of an ammonia concentration is high.

As above, according to the above aspect, an ammonia sensor element which can detect an ammonia concentration in gas with high accuracy can be provided.

The embodiments of the present invention have been described as above, however, the present invention is not limited to each of the above embodiments, and can be applied to various embodiments within the scope not departing from the gist thereof.

EXPLANATIONS OF LETTERS OR NUMERALS

1: ammonia sensor element
2: measured gas chamber
3: reference gas chamber
4: solid electrolyte body
45: first proton conducting solid electrolyte
5: detection electrode
55: second proton conducting solid electrolyte
6: reference electrode

The invention claimed is:
1. An ammonia sensor element comprising:
a measured gas chamber to which a measured gas is introduced;
a reference gas chamber to which a reference gas is introduced;
a solid electrolyte body arranged between the measured gas chamber and the reference gas chamber and having a first main surface facing the measured gas chamber and a second main surface facing the reference gas chamber;
a detection electrode formed on the first main surface of the solid electrolyte body; and
a reference electrode formed on the second main surface of the solid electrolyte body,
wherein the solid electrolyte body contains a first proton conducting solid electrolyte,
the detection electrode contains a second proton conducting solid electrolyte,
the second proton conducting solid electrolyte has an acid strength greater than that of the first proton conducting solid electrolyte, the second proton conducting solid electrolyte comprises at least one phosphoric acid-based compound selected from a group consisting of lanthanum phosphate, tin pyrophosphate, zirconium pyrophosphate, and tin phosphate, and the detection electrode further contains perovskite-type oxide.

2. The ammonia sensor element according to claim 1, wherein the first proton conducting solid electrolyte is made of perovskite-type oxide.

3. The ammonia sensor element according to claim 1, wherein the detection electrode further contains a metal, and the detection electrode has a structure in which the second proton conducting solid electrolyte and the metal are mutually three dimensionally intermixed.

4. The ammonia sensor element according to claim 3, wherein the detection electrode has an electrode base layer containing the first proton conducting solid electrolyte, formed on the solid electrolyte body and an electrode surface layer containing the second proton conducting solid electrolyte, formed on the electrode base layer.

5. The ammonia sensor element according to claim 4, wherein the thickness t of the detection electrode, the thickness $t_b$ of the electrode base layer and the thickness $t_s$ of the electrode layer satisfy the relations of the following formula (1) and the following formula (2):

$$t = t_b + t_s \quad (1)$$

$$0.1 \leq t_s/t_b \leq 1 \quad (2).$$

6. The ammonia sensor element according to claim 1, wherein the detection electrode has an electrode base layer containing the first proton conducting solid electrolyte, formed on the solid electrolyte body and an electrode surface layer containing the second proton conducting solid electrolyte, formed on the electrode base layer.

7. The ammonia sensor element according to claim 6, wherein the thickness t of the detection electrode, the thickness to of the electrode base layer and the thickness is of the electrode layer satisfy the relations of the following formula (1) and the following formula (2):

$$t = t_b + t_s \quad (1)$$

$$0.1 \leq t_s/t_b \leq 1 \quad (2).$$

8. The ammonia sensor element according to claim 1, wherein the perovskite-type oxide contained in the detection electrode comprises at least one selected from the group consisting of strontium zirconate, calcium zirconate, barium zirconate, strontium cerate, calcium cerate, and barium cerate, those being doped with rare-earth elements.

* * * * *